(12) United States Patent
Lee et al.

(10) Patent No.: US 7,572,644 B2
(45) Date of Patent: Aug. 11, 2009

(54) HYDROGEL COPOLYMER, SUBSTRATE COATED WITH THE COPOLYMER, METHOD OF PRODUCING MICROARRAY USING THE COPOLYMER, AND MICROARRAY PRODUCED BY THE METHOD

(75) Inventors: In-ho Lee, Yongin-si (KR); Jun-hong Min, Yongin-si (KR); Su-hyeon Kim, Seoul (KR)

(73) Assignee: Samsung Electronics Co., Ltd. (KR)

( * ) Notice: Subject to any disclaimer, the term of this patent is extended or adjusted under 35 U.S.C. 154(b) by 270 days.

(21) Appl. No.: 11/334,145

(22) Filed: Jan. 17, 2006

(65) Prior Publication Data

US 2006/0160120 A1    Jul. 20, 2006

(30) Foreign Application Priority Data

Jan. 14, 2005    (KR) .................... 10-2005-0003637

(51) Int. Cl.
*G01N 33/547* (2006.01)
*G01N 33/544* (2006.01)
*G01N 33/53* (2006.01)
*C12M 1/34* (2006.01)
*C07K 1/14* (2006.01)
*C07D 207/00* (2006.01)

(52) U.S. Cl. ................ 436/532; 435/7.1; 435/7.92; 435/287.1; 435/287.2; 435/287.9; 436/72; 436/518; 436/528; 530/405; 530/406; 530/412; 548/550; 524/916

(58) Field of Classification Search ................ 436/528, 436/72, 518, 532; 548/550; 564/123; 568/558; 524/916; 424/487; 435/7.1, 7.92, 287.1, 435/287.2, 287.9; 530/405, 406, 412
See application file for complete search history.

(56) References Cited

U.S. PATENT DOCUMENTS 5,336,797 A * 8/1994 McGee et al. ............... 556/419
6,174,683 B1   1/2001 Hahn et al. .................... 435/6

* cited by examiner

*Primary Examiner*—Shafiqul Haq
(74) *Attorney, Agent, or Firm*—Cantor Colburn LLP

(57) ABSTRACT

A novel hydrogel copolymer, a substrate coated with the copolymer, a method of producing a microarray using the copolymer, and a microarray produced by the method are provided. The use of the hydrogel copolymer makes efficient removal of protein and high integration of nucleic acid and protein on a substrate for a microarray possible.

40 Claims, 3 Drawing Sheets

HYDROGEL COPOLYMER, SUBSTRATE COATED WITH THE COPOLYMER, METHOD OF PRODUCING MICROARRAY USING THE COPOLYMER, AND MICROARRAY PRODUCED BY THE METHOD

CROSS-REFERENCE TO RELATED PATENT APPLICATION

This application claims the benefit of Korean Patent Application No. 10-2005-0003637, filed on Jan. 14, 2005, in the Korean Intellectual Property Office, the disclosure of which is incorporated herein in its entirety by reference.

BACKGROUND OF THE INVENTION

1. Field of the Invention

The present invention relates to a novel hydrogel copolymer, a substrate coated with the copolymer, a method of producing a microarray using the copolymer, and a microarray produced by the method.

2. Description of the Related Art

In a microarray, certain molecules are immobilized within discrete known regions on a substrate. Examples of such a microarray include polynucleotide and protein microarrays. The microarray is made using a method of sequentially synthesizing a probe material on a substrate or a spotting method in which a previously-synthesized probe material is immobilized on an activated substrate.

In a spotting method, a microarray is made by coating a linker material (e.g. GAPS (gamma-aminopropyltriethoxy silane) and GAPDES (gamma-aminopropyldiethoxy silane), etc.) having a reactive functional group, for example, an amino group, on a substrate and reacting the functional group with a probe material to immobilize the probe material on the substrate, or by coating a linker material on a substrate, activating the linker material, for example, modifying the linker material using N-hydroxysuccinimide (NHS) into a highly reactive material, and reacting the linker material with a probe material having the reactive functional group such as an amino group. Examples of compounds conventionally used as the linker material include an alkylsilane having a carboxylic group and an alkyl sulfur compound having a carboxylic group. These compounds contain silicon or sulfur, and thus can bind to a $SiO_2$ or Au substrate, and have a carboxylic group, and thus can be easily activated.

According to the conventional technology, a linker material can react with a probe material after being coated on a substrate and activated. Thus, reaction efficiency is low and uniform activation cannot be achieved. In addition, a conventional linker material includes a hydrophobic portion such as an alkyl group. Thus, in a method in which signals generated by a reaction between a probe material and a target material on a microarray manufactured using the conventional linker material are measured and analyzed, the analysis efficiency is poor due to a strong signal generated by non-specific binding of the target material to a background portion, i.e., a strong noise.

U.S. Pat. No. 6,174,683 discloses a method of rapidly and inexpensively producing a biochip using a polyurethane-based hydrogel in order to immobilize a probe material on a substrate. Although this method includes the use of hydrogel having polyethyleneoxide (PEO) as a backbone, there is no description regarding high integration of a probe material using poly[N-isopropylacrylamide] of the present invention.

The inventors of the present invention made efforts to solve the problems of the conventional technology and found a compound capable of achieving high integration of a probe material when it is coated on the substrate and being used to produce a microarray.

SUMMARY OF THE INVENTION

The present invention provides a hydrogel copolymer capable of achieving high integration of a probe material on a substrate when it is coated on the substrate.

The present invention also provides a method of selectively removing a material having an amino group using a substrate coated with the copolymer.

The present invention also provides a substrate for a microarray, which is coated with the copolymer.

The present invention also provides a microarray in which biomolecules are immobilized on the copolymer.

The present invention also provides a method of producing a microarray using the copolymer.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
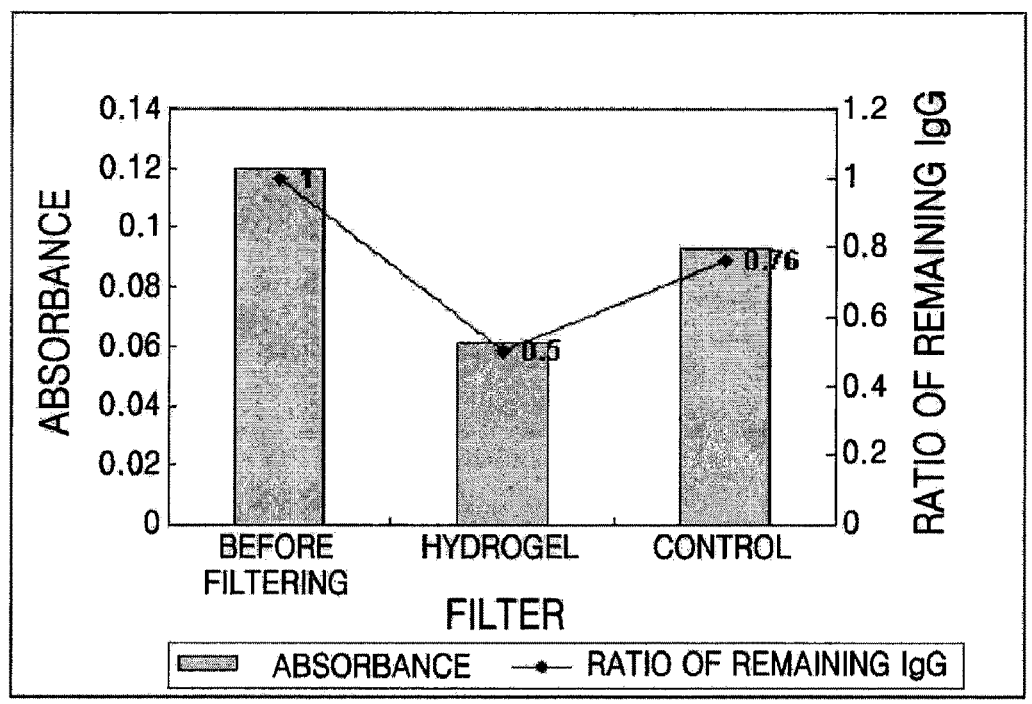
FIG. 1 is a graph illustrating the IgG removal efficiency using a hydrogel copolymer of the present invention.

The present invention provides a hydrogel copolymer including repeat units represented by formulae (1) and (2):

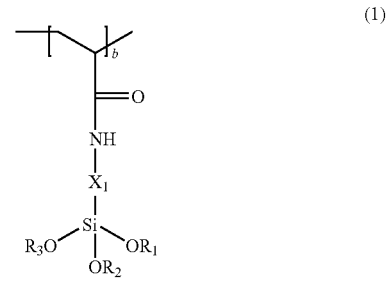

where $X_1$ is a single bond, O, S, a substituted or unsubstituted alkylene group of 1-20 carbon atoms, a substituted or unsubstituted heteroalkylene group of 1-20 carbon atoms, a substituted or unsubstituted alkenylene group of 2-20 carbon atoms, a substituted or unsubstituted heteroalkenylene group of 2-20 carbon atoms, or a substituted or unsubstituted arylene group of 6-30 carbon atoms; $R_1$, $R_2$ and $R_3$ are each independently a hydrogen atom, a halogen atom, a hydroxy group, a substituted or unsubstituted alkyl group of 1-20 carbon atoms, a substituted or unsubstituted alkoxy group of 1-20 carbon atoms, a substituted or unsubstituted alkenyl group of 1-20 carbon atoms, a substituted or unsubstituted aryl group of 6-30 carbon atoms, a substituted or unsubstituted aryloxy group of 6-30 carbon atoms, a substituted or unsubstituted heteroaryl group of 2-30 carbon atoms, or a substituted or unsubstituted heteroaryloxy group of 2-30 carbon atoms; and b is an integer from 10 to 100,000,

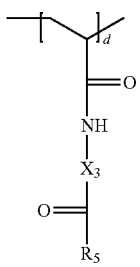
(2)

where $X_3$ is a single bond, O, S, a substituted or unsubstituted alkylene group of 1-20 carbon atoms, a substituted or unsubstituted heteroalkylene group of 1-20 carbon atoms, a substituted or unsubstituted alkenylene group of 2-20 carbon atoms, a substituted or unsubstituted heteroalkenylene group of 2-20 carbon atoms, or a substituted or unsubstituted arylene group of 6-30 carbon atoms; $R_5$ is

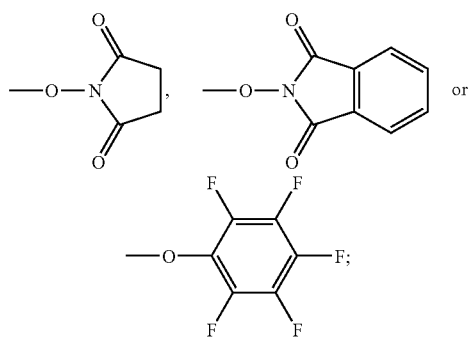

and d is an integer from 10 to 100,000.

The hydrogel copolymer may further include a repeat unit represented by formula (3):

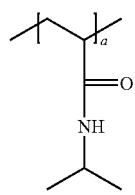
(3)

where a is an integer from 10 to 100,000.

The hydrogel copolymer may further include a repeat unit represented by formula (4):

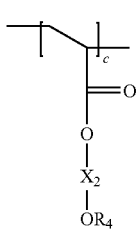
(4)

where $X_2$ is a single bond, O, S, a substituted or unsubstituted alkylene group of 1-20 carbon atoms, a substituted or unsubstituted heteroalkylene group of 1-20 carbon atoms, a substituted or unsubstituted alkenylene group of 2-20 carbon atoms, a substituted or unsubstituted heteroalkenylene group of 2-20 carbon atoms, or a substituted or unsubstituted arylene group of 6-30 carbon atoms; $R_4$ is a hydrogen atom, a halogen atom, a hydroxy group, a substituted or unsubstituted alkyl group of 1-20 carbon atoms, a substituted or unsubstituted alkoxy group of 1-20 carbon atoms, a substituted or unsubstituted alkenyl group of 1-20 carbon atoms, a substituted or unsubstituted aryl group of 6-30 carbon atoms, a substituted or unsubstituted aryloxy group of 6-30 carbon atoms, a substituted or unsubstituted heteroaryl group of 2-30 carbon atoms, or a substituted or unsubstituted heteroaryloxy group of 2-30 carbon atoms; and c is an integer from 10 to 100,000.

The present invention also provides a hydrogel copolymer including repeat units represented by formulae (1) to (4):

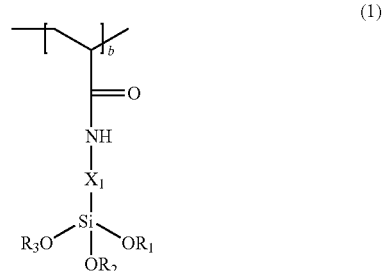
(1)

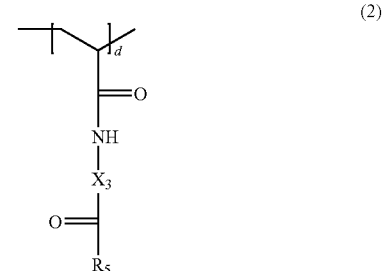
(2)

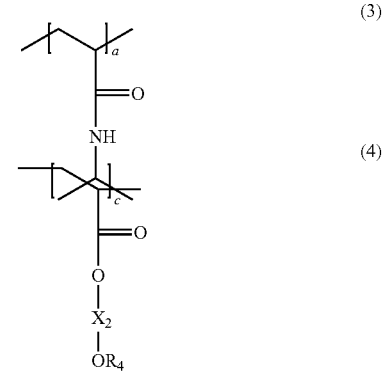
(3)

(4)

where $X_1$, $X_2$, $X_3$, $R_1$, $R_2$, $R_3$, $R_4$, $R_5$, a, b, c and d are as defined above.

The alkyl group as used herein refers to a linear or branched radical having 1-20 carbon atoms, preferably a linear or branched radical having 1-12 carbon atoms, and more preferably a lower alkyl having 1-6 carbon atoms. Examples of the alkyl group include methyl, ethyl, n-propyl, isopropyl, n-butyl, isobutyl, sec-butyl, t-butyl, pentyl, iso-amyl, and hexyl. A lower alkyl radical having 1-3 carbon atoms is more preferable.

The alkoxy group as used herein refers to an oxygen-containing linear or branched alkyl radical having 1-20 carbon atoms. A lower alkoxy radical having 1-6 carbon atoms is preferable. Examples of the lower alkoxy radical include methoxy, ethoxy, propoxy, butoxy, and t-butoxy. A lower alkoxy radical having 1-3 carbon atoms is more preferable. The alkoxy radical may be substituted by one or more halo atoms such as fluoro, chloro, or bromo, to give a haloalkoxy radical. A lower haloalkoxy radical having 1-3 carbon atoms is more preferable. Examples of the haloalkoxy radical include fluoromethoxy, chloromethoxy, trifluoromethoxy, trifluoroethoxy, fluoroethoxy, and fluoropropoxy.

The alkenyl group as used herein refers to a linear or branched aliphatic hydrocarbon group containing a carbon-carbon double bond and 2-30 carbon atoms. Preferably, the alkenyl group has 2-12 carbon atoms, and more preferably 2-6 carbon atoms. The "branched alkenyl group" refers to one or more lower alkyl or alkenyl groups appended to a linear alkenyl group. The alkenyl group may be unsubstituted or substituted by one or more non-limiting substituents selected from halo, carboxy, hydroxy, formyl, sulfo, sulfino, carbamoyl, amino, and imino. Examples of the alkenyl group include ethenyl, propenyl, carboxyethenyl, carboxypropenyl, sulfinoethenyl, and sulfonoethenyl.

The aryl group as used herein, which is used alone or in combination, refers to a carbocyclic aromatic system of 6-20 carbon atoms having one or more rings. The rings may be attached to each other as a pendant group or may be fused. The term "aryl" includes an aromatic radical such as phenyl, naphthyl, tetrahydronaphthyl, indane, and biphenyl. Phenyl is more preferable. The aryl group may have 1-3 substituents such as hydroxy, halo, haloalkyl, nitro, cyano, alkoxy, and lower alkylamino. The aryloxy group as used herein refers to aryl-O—. The definition of the "aryl" in the aryloxy group is as described above.

The heteroaryl group as used herein refers to a monovalent monocyclic or bicyclic aromatic radical of 6-20 carbon atoms containing one, two or three hetero atoms selected from N, O and S. The term "heteroaryl" also means a monovalent monocyclic or bicyclic aromatic radical forming N-oxide or a quaternary salt by oxidation or quaternization of a heteroatom in the ring. Examples of such heteroaryl include, but are not limited to, thienyl, benzothienyl, pyridyl, pyrazinyl, pyrimidinyl, pyridazinyl, quinolinyl, quinoxalinyl, imidazolyl, furanyl, benzofuranyl, thiazolyl, isoxazolyl, benzisoxazolyl, benzimidazolyl, triazolyl, pyrazolyl, pyrrolyl, indolyl, 2-pyridonyl, 4-pyridonyl, N-alkyl-2-pyridonyl, pyrazinonyl, pyridazinonyl, pyrimidinonyl, oxazolonyl, and their equivalent N-oxides (e.g., pyridyl N-oxide, quinolinyl N-oxide), and quaternary salts thereof.

The heteroaryloxy group as used herein refers to heteroaryl-O—. The definition of the "heteroaryl" in the heteroaryloxy group is as described above.

The hydrogel copolymer includes a silane moiety capable of easily binding to a solid substrate, a hydrophilic poly[N-isopropylacrylamide] moiety increasing the hydrophilicity of molecule, and an activated functional moiety capable of causing a coupling reaction with a functional group such as an amino group. Examples of the solid substrate include glass, a silicon wafer, plastic, polystyrene, a membrane, and a metal plate, but are not limited thereto. The shape of the solid substrate is not particularly limited and may be a flat shape, a nanoparticle shape, or a channel shape.

The activated functional moiety includes a good leaving group that is substituted in the coupling reaction and a functional group for activating the good leaving group. The good leaving group is, for example,

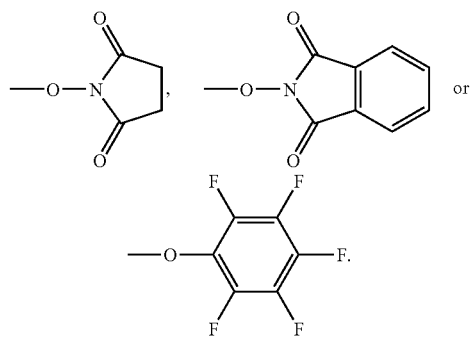

The functional group for activating the good leaving group is derived from dicarboxylate.

The hydrogel copolymer of the present invention has the moiety capable of easily binding to a substrate and the good leaving group, and thus can be used as a linker material when a material is immobilized on a substrate. In this case, the poly[N-isopropylacrylamide] moiety in the hydrogel copolymer is very hydrophilic, and thus can prevent a target material from non-specifically binding to a background portion when an immobilized material and the target material interact with each other. In addition, since the hydrogel copolymer of the present invention includes the moiety capable of easily binding to a substrate and the good leaving group, the coating process of the compound on the substrate and the coupling process of a material to be immobilized can be continuously carried out using one compound.

The present invention also provides a method of selectively removing a material having an amino group from a sample, the method including: coating the hydrogel copolymer on a substrate having nanopores; reacting the hydrogel copolymer with the sample including the material having the amino group; and eluting an unreacted sample.

When the hydrogel copolymer is coated on a substrate having nanopores, a silane moiety of the hydrogel copolymer forms a covalent bond with the substrate. When a sample including a material having an amino group contacts the hydrogel copolymer bound to the substrate, an activated functional moiety, such as N-hydroxysuccinimidyl (NHS) ester, of the hydrogel copolymer reacts with an amino group of a material having the amino group such as protein, thereby causing the good leaving group to leave and form a peptide bond. After a material having the amino group such as protein is bound to the hydrogel copolymer, unreacted nucleic acids such as DNA can be eluted using an eluent. In a cell or virus lysis, the lysate includes proteins, nucleic acids, etc. In this case, to isolate nucleic acids, removal of proteins is required. Thus, the method of the present embodiment enables nucleic acids to be efficiently isolated by removing proteins from the cell lysate, and thus it can be suitable for the implementation of Lab-on-a-Chip (LOC). This can be performed by shrinkage of the hydrogel copolymer in which only DNA passes through the substrate coated with the hydrogel copolymer and proteins, antibody, antigen, etc., do not pass through the substrate due to the formation of a covalent bond with the activated functional moiety of the hydrogel copolymer.

The present invention also provides a substrate for a microarray, coated with the hydrogel copolymer.

Examples of the substrate include glass, a silicon wafer, plastic, polystyrene, a membrane, and a metal plate, but are not limited thereto. The shape of the substrate is not particularly limited, and may be a flat shape, a nanoparticle shape, or a channel shape. The coating process is generally performed in the production of a microarray and any coating method conventionally known in the art can be used in the present invention. For example, the coating can be achieved using a method selected from the group consisting of a self assembled thin film coating method, a spin coating method, a dipping method, a spraying method, a printing method, and a Langmuir Blodget (LB) method. The coating of the hydrogel copolymer on the substrate is achieved through a reaction between alkoxysilane and an OH group on the substrate. Those skilled in the art can perform the reaction using the above-described coating methods under appropriate conditions.

The present invention also provides a microarray in which biomolecules are immobilized on the hydrogel copolymer on a substrate. The biomolecules may be proteins or nucleic acids, and thus the microarray of the present embodiment may be a protein or polynucleotide microarray.

The present invention also provides a method of producing a microarray, the method including: coating the hydrogel copolymer on a substrate; and coupling the coated hydrogel copolymer and biomolecules to immobilize the biomolecules on the substrate.

Examples of the substrate include glass, a silicon wafer, plastic, polystyrene, a membrane and a metal plate, but are not limited thereto. The shape of the substrate is not particularly limited, and may be a flat shape, a nanoparticle shape, or a channel shape. The coating process is generally performed in the production of a microarray and any coating method conventionally known in the art can be used in the present invention. For example, the coating can be achieved using a method selected from the group consisting of a self assembled thin film coating method, a spin coating method, a dipping method, a spraying method, a printing method and a Langmuir Blodget (LB) method. The coating of the hydrogel copolymer on the substrate is achieved through a reaction between alkoxysilane and an OH group on the substrate. Those skilled in the art can perform the reaction using the above-described coating methods under appropriate conditions.

The coupling is achieved by reacting the good leaving group, for example,

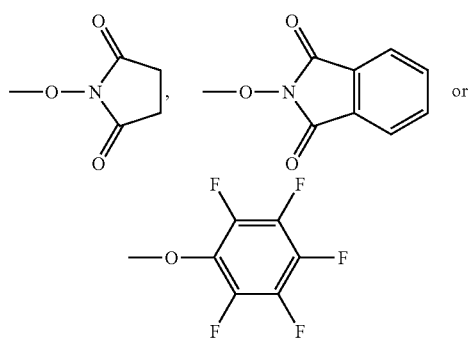

of the hydrogel copolymer coated on the substrate with a reactive group, for example, an amino group, of biomolecules to substitute the good leaving group with the biomolecule. The biomolecule means a material immobilized on a substrate, which can specifically bind to a target material. In the present invention, examples of the biomolecule include proteins, nucleic acids and polysaccharides, but are not limited thereto. Preferably, the biomolecule is proteins or nucleic acids.

The present invention will now be described in greater detail with reference to the following examples. The following examples are for illustrative purposes only and are not intended to limit the scope of the invention.

EXAMPLE 1

Synthesis of Hydrogel Copolymer of the Present Invention

Step 1: Synthesis of 6-acryloylamino-hexanoic acid (1)

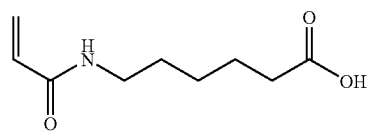

Sodium hydroxide (7.6 g, 190 mmol) and 6-aminohexanoic acid (10 g, 76 mmol) were dissolved in distilled water (50 mL) at room temperature. Acryloyl chloride (8.24 g, 91 mmol) in dry $CH_2Cl_2$ (50 mL) was slowly added to the mixture at room temperature. The resulting mixture was stirred at room temperature for 10 h. The reaction was quenched by adding 10% HCl (20 mL, pH 3) at room temperature and the mixture was extracted with ethyl acetate (2×100 mL). The combined organic layers were dried over $MgSO_4$ and concentrated to give a product as a white solid (11.6 g, 82%). This compound was used without further purification.

$^1$H-NMR (300 MHz, $CDCl_3$): δ 1.40 (m, 2H), 1.59 (m, 4H), 2.37 (t, J=7.2 Hz, 2H), 3.48 (q, J=6.9 Hz, 2H), 5.63 (dd, J=10.2 Hz, J=1.5 Hz, 1H), 5.78 (s, NH—, 1H), 6.10 (dd, J=17.1 Hz, J=10.5 Hz, 1H), 6.28 (dd, J=17.1 Hz, J=1.5 Hz, 1H).

Step 2: Synthesis of 6-acryloylamino-hexanoic acid 2,5-dioxo-pyrrolydin-1-yl ester (2)

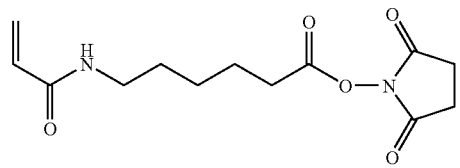

N-hydroxysuccinimide (3.34 g, 29 mmol) and 6-acryloylamino-hexanoic acid (1, 5 g, 27 mmol) were dissolved in dry $CH_2Cl_2$ (100 mL) at room temperature. A solution of N,N'-dicyclohexylcarbodiimide (DCC) (5.98 g, 29 mmol) in dry $CH_2Cl_2$ (20 mL) was slowly added to the mixture at 0° C. The resulting mixture was stirred at room temperature for 4 h. The solid residue was filtered through a sintered glass filter and the filtrate was concentrated to give a product as a white solid (6.3 g, 84%). Purification of the crude product by column chromatograpy [Hex:EA=1:2 (+10% MeOH)] gave the product as a white solid. (6.1 g, 80%)

$^1$H-NMR (300 MHz, $CDCl_3$): δ 1.5 (m, 4H), 1.59 (m, 2H), 2.63 (t, J=7.2 Hz, 2H), 2.85 (s, J=4H), 3.36 (q, J=6 Hz, 2H), 5.63 (dd, J=10.2 Hz, J=1.5 Hz, 1H), 6.10 (dd, J=17.1 Hz, J=10.5 Hz, 1H), 6.28 (dd, J=17.1 Hz, J=1.5 Hz, 1H).

Step 3: Synthesis of
3-(triethoxysilyl)propylacrylamide (3)

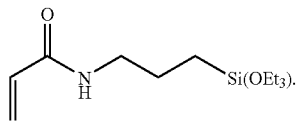

3-Aminopropyltriethoxysilane (1.5 g, 6.78 mmol) and triethylamine (1.03 g, 10.17 mmol) were dissolved in dry THF (7 mL) at 0° C. under nitrogen atmosphere. Acryloyl chloride (0.92 g, 10.17 mmol) in dry THF (7 mL) was slowly added to the mixture at 0° C. The resulting mixture was stirred at 0° C. for 10 h. The resulting mixture was filtered through a sintered glass filter and the filtrate was concentrated to give a product as a red oil (1.31 g, 70%). This compound was used without further purification.

$^1$H-NMR (300 MHz, CDCl$_3$): δ 0.65 (t, J=7.8 Hz, 2H), 1.23 (t, J=7.2 Hz, 9H), 1.57 (m, 2H), 3.33 (q, J=6 Hz, 2H), 3.82 (q, J=6.9 Hz, 6H), 5.60 (dd, J=9.9 Hz, J=1.5 Hz, 1H), 6.12 (dd, J=17.1 Hz, J=9.9 Hz, 1H), 6.25 (dd, J=17.1 Hz, J=1.5 Hz, 1H).

Step 4: Synthesis of Random Copolymer (4)

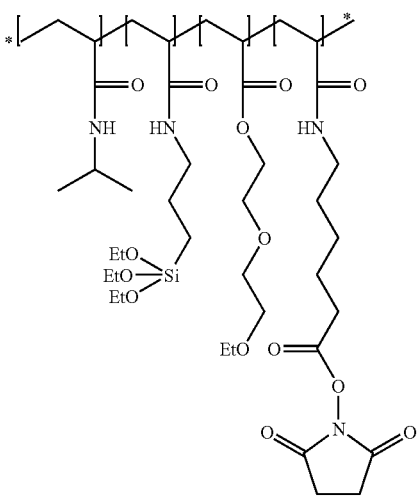

6-Acryloylamino-hexanoic acid 2,5-dioxo-pyrrolidin-1-yl ester (2, 0.71 g, 2.5 mmol), 3-(triethoxysilyl)propylacrylamide (3, 0.69 g, 2.5 mmol), N-isopropylacrylamide (1.42 g, 12.5 mmol), di(ethyleneglycol)ethyl ether acrylate (2.35 g, 12.5 mmol) and N,N'-azobisisobutyronitrile (AIBN, 0.59 g, 3 mmol) were dissolved in dry toluene (80 mL) at room temperature under nitrogen atmosphere. The mixture was stirred at 80° C. for 20 h. The resulting mixture was dripped into hexane (500 ml) at room temperature to precipitate the polymer. The resulting precipitates were collected by filtration and dried in vacuum to give the desired polymer as a pale yellow solid (2 g, 40%).

EXAMPLE 2

Removal of Proteins Using Hydrogel Copolymer

To identify whether the hydrogel copolymer synthesized in Example 1 efficiently removed proteins from a sample including nucleic acids and proteins, the hydrogel coplymer was coated on a filter paper. The filter paper (pore size: 3 μm) was coated with the hydrogel copolymer and a Cy3 tagged DNA (500-mer) and a Cy3 tagged IgG were filtered through the coated filter paper. The relative amounts of Cy3 tagged DNA and IgG were determined by measuring the absorbance at 530 nm after passing them through the filter paper. In a control group, an uncoated filter paper was used. The results were shown in the following Table.

| | | | |
|---|---|---|---|
| DNA | DNA solution | 0.067 | |
| | Hydrogel filter | 0.066 | 1.5% removal |
| | Control | 0.066 | 1.5% removal |
| Protein (IgG) | IgG solution | 0.120 | — |
| | Hydrogel filter | 0.061 | 50% removal |
| | Control | 0.093 | 24% removal |

FIG. 1 is a graph illustrating the IgG removal efficiency using the hydrogel copolymer of the present invention. As is apparent from the above Table and FIG. 1, the filter coated with the hydrogel copolymer showed a very low removal rate for DNA of 1.5%, whereas it showed a very high removal rate for IgG of 50%. In the case of the control group in which an uncoated filter paper was used, the IgG removal rate was 24%. The hydrogel filter of the present invention showed 2 times higher protein removal rate than the control group.

Thus, it can be seen that using the hydrogel copolymer of the present invention, proteins can be removed from cell lysate including nucleic acids and proteins after cell lysis to efficiently isolate nucleic acids.

EXAMPLE 3

Production of Substrate Coated with Hydrogel Copolymer

Figure 4:
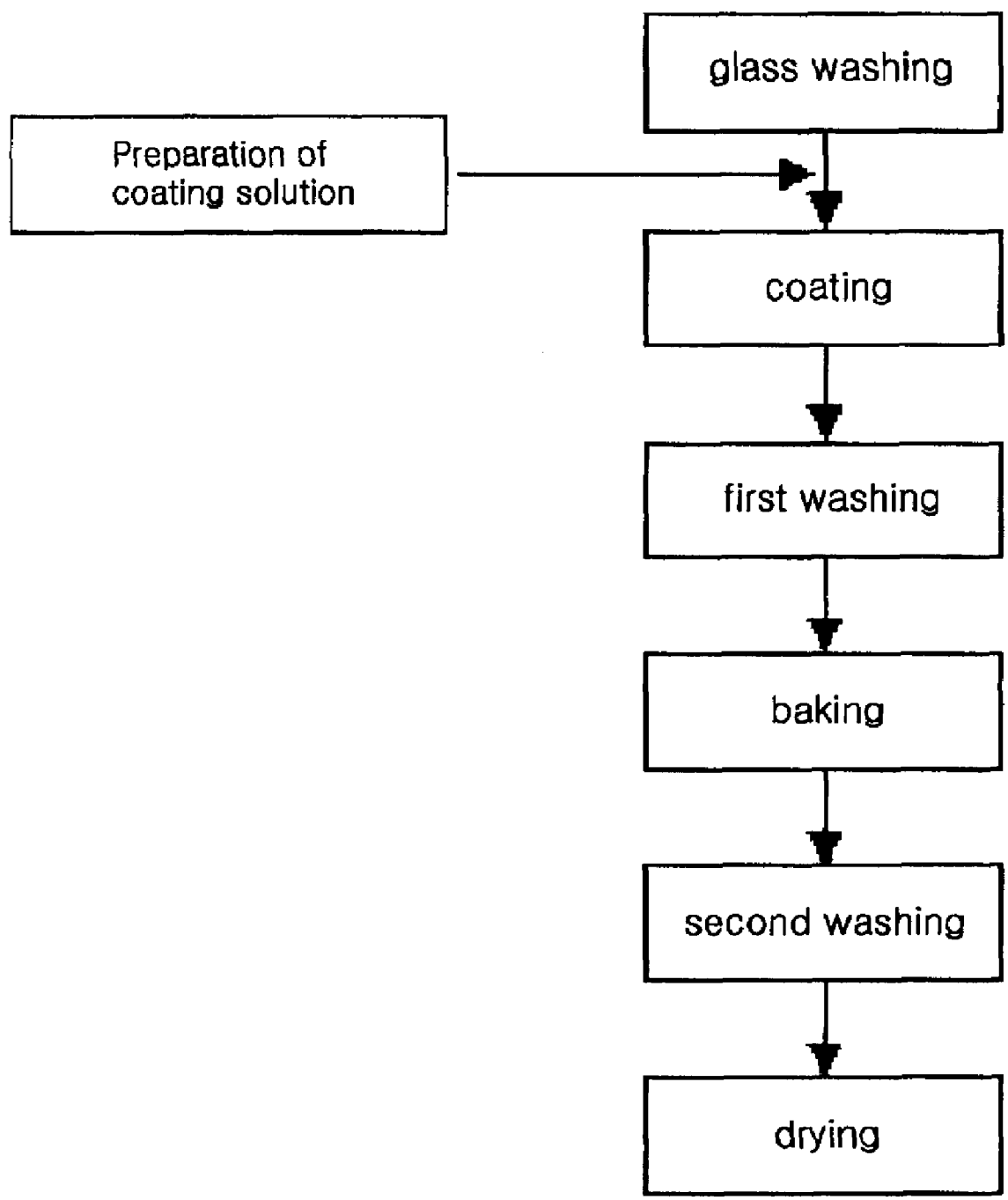
FIG. 4 is a flow chart of an embodiment of the process of producing the substrate.

A substrate for a microarray was produced using the hydrogel coplymer of the present invention. The process of producing the substrate is illustrated in FIG 4.

1. Glass Washing

A 25×75 mm slide glass (#2948, Corning, USA) was used as a substrate for immobilizing biomolecules. Since it was important that dust, contaminants (organic materials, inorganic materials), etc. attached to the glass surface were removed before coating, the slide glass was first washed with deionized water to remove dust, and then was dipped in a 3:1 mixture (piranha solution) of a H$_2$SO$_4$ solution and a H$_2$O$_2$ solution for 1 h to remove contaminants. Next, deionized water was sufficiently flowed to remove the piranha solution remained on the surface, and then ultrasonic washing was performed in an acetone solution and an isopropyl alcohol solution for 5 min, respectively. Thereafter, the washed glass substrate was dried using a spin dryer.

2. Preparation of Coating Solution

Dimethylformamide (DMF), ethanol, toluene, etc. were used as a solvent of a coating solution. A solvent having best coating characteristics among these solvents was ethanol. 1% (w/w) of the hydrogel copolymer was mixed with ethanol to prepare a coating solution.

3. Coating (Self-Assembled Thin Film Coating)

This is a step of coating a hydrogel linker capable of reacting with proteins, DNA, etc., on the washed glass surface. The coating was achieved by dipping the washed glass in the hydrogel coating solution at room temperature for 1 h.

4. First Washing

This is a step of removing the unreacted coating solution remained on the coated hydrogel substrate. To allow the covalently bound coating material to be uniformly coated on the substrate as a monolayer and impurities to be removed, the coated substrate was immersed in an ethanol solution and stirred for 5 min. After washing, the substrate was dried with a spin drier so as to produce no stain.

5. Baking

To improve the binding force of the hydrogel linker covalently bound to the glass substrate, the glass substrate was hardened in an oven at 110° C. for 45 min.

6. Second Washing and Drying

The washing process was performed by dipping and stirring the baked substrate in an ethanol solution for 5 min to thoroughly remove the coating material which was not chemically bound to the hydrogel-coated substrate, impurities, etc. The substrate was dried by evaporating the ethanol remained on the surface using a spin dryer.

EXAMPLE 4

Immobilization of Nucleic Acid Using Substrate Coated with Hydrogel Copolymer

Figure 2:
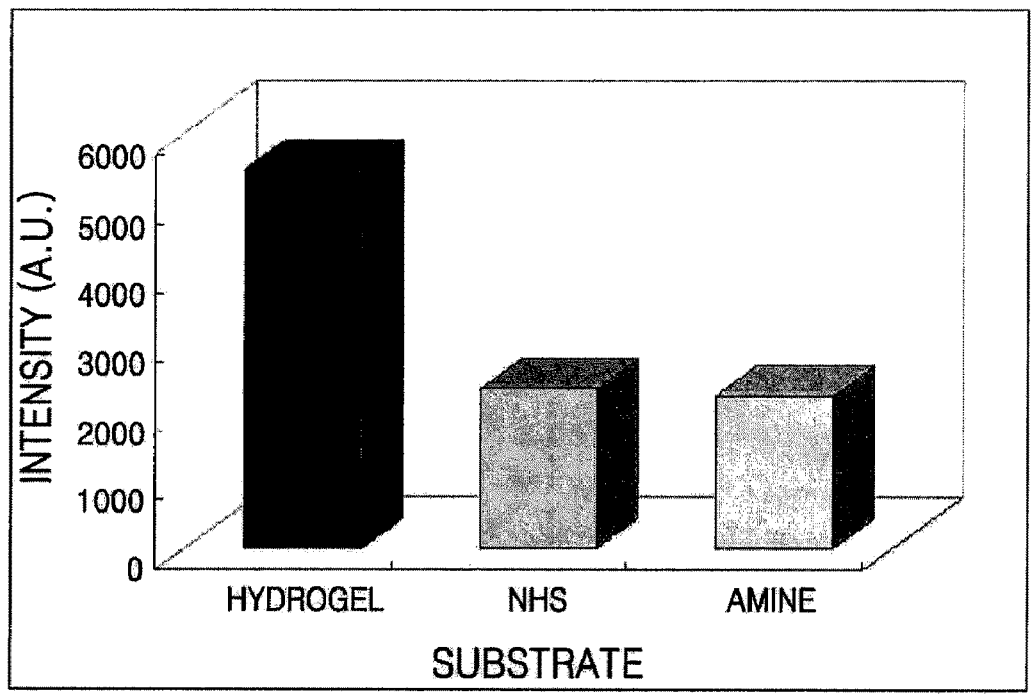
FIG. 2 is a graph illustrating the fluorescence intensity of Cy3 tagged human IgG bound to each of substrates coated with an aptamer, which is measured with a laser scanner.

To identify whether the substrate coated with the hydrogel copolymer efficiently immobilized nucleic acids, an aptamer as a DNA probe was immobilized on the substrate. The immobilization of the aptamer on the substrate was achieved using a conventional immobilization technique. The used aptamer was an aptamer (70-mer, 1.4 µM) specific to Fc of IgG and an assay protein specifically binding to the aptamer was Cy3 tagged human IgG (10 µg/ml). The substrate coated with the hydrogel copolymer of the present invention, a substrate coated with NHS (Lab made) and an amine substrate (Corning) were used. The assay protein was bound to each of the coated substrates, and then the fluorescence intensity was measured using a laser scanner. FIG. 2 is a graph illustrating the fluorescence intensity of the Cy3 tagged human IgG bound to each of the substrates coated with the aptamer. Referring to FIG. 2, it can be seen that the substrate coated with the hydrogel copolymer of the present invention has about 1.30 times higher nucleic acid immobilization ability than the substrate coated with NHS.

Thus, when using the substrate coated with the hydrogel copolymer of the present invention, high integration of nucleic acid can be achieved.

EXAMPLE 5

Immobilization of Protein Using Substrate Coated with Hydrogel Copolymer

Figure 3:
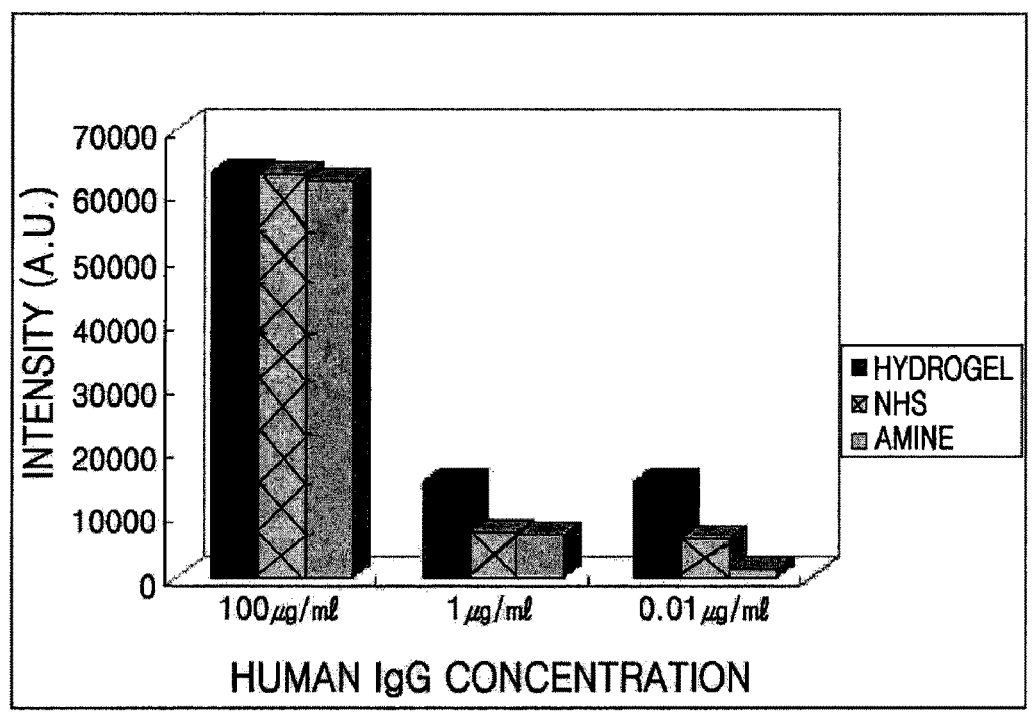
FIG. 3 is is a graph illustrating the fluorescence intensity of Cy3 tagged human IgG immobilized on each of substrates, which is measured with a laser scanner.

To identify whether the substrate coated with the hydrogel copolymer efficiently immobilized proteins, an IgG probe was immobilized on the substrate. The immobilization of the IgG probe on the substrate was achieved using a conventional immobilization technique. 100 µg/ml, 1 µg/ml and 0.01 µg/ml of Cy3 tagged human IgG were used. The substrate coated with the hydrogel copolymer of the present invention, a substrate coated with NHS (Lab made) and an amine substrate (Corning) were used. The fluorescence intensity of the Cy3 tagged human IgG immobilized on each of the coated substrates was measured using a laser scanner. FIG. 3 is a graph illustrating the fluorescence intensity of the Cy3 tagged human IgG immobilized on each of the substrates. Referring to FIG. 3, it can be seen that the substrate coated with the hydrogel copolymer of the present invention has 1.22 and 11.60 times higher protein immobilization ability than the amine substrate in the cases of 1 µg/ml and 0.01 µg/ml of the Cy3 tagged human IgG, respectively.

Thus, when using the substrate coated with the hydrogel copolymer of the present invention, high integration of protein can be achieved.

As described above, the use of the hydrogel copolymer of the present invention makes efficient removal of protein and high integration of nucleic acid and protein on a substrate for a microarray possible.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A hydrogel copolymer comprising repeat units represented by formulae (1) and (2):

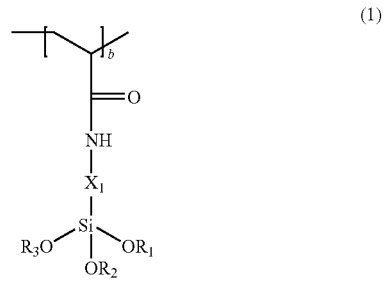

(1)

where $X_1$ is a single bond, O, S, a substituted or unsubstituted alkylene group of 1-20 carbon atoms, a substituted or unsubstituted heteroalkylene group of 1-20 carbon atoms, a substituted or unsubstituted alkenylene group of 2-20 carbon atoms, or a substituted or unsubstituted arylene group of 6-30 carbon atoms; $R_1$, $R_2$ and $R_3$ are each independently a hydrogen atom, a halogen atom, a hydroxy group, a substituted or unsubstituted alkyl group of 1-20 carbon atoms, a substituted or unsubstituted alkoxy group of 1-20 carbon atoms, a substituted or unsubstituted alkenyl group of 1-20 carbon atoms, a substituted or unsubstituted aryl group of 6-30 carbon atoms, a substituted or unsubstituted aryloxy group of 6-30 carbon atoms, a substituted or unsubstituted heteroaryl group of 2-30 carbon atoms, or a substituted or unsubstituted heteroaryloxy group of 2-30 carbon atoms; and b is an integer from 10 to 100,000,

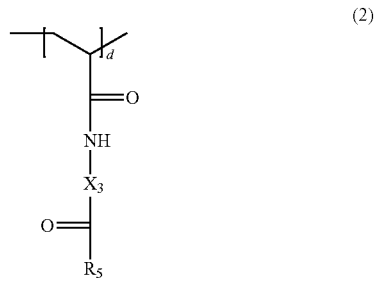

(2)

where $X_1$ is a single bond, O, S, a substituted or unsubstituted alkylene group of 1-20 carbon atoms, a substituted or unsubstituted heteroalkylene group of 1-20 carbon atoms, a substituted or unsubstituted alkenylene group of 2-20 carbon atoms, a substituted or unsubstituted heteroalkenylene group of 2-20 carbon atoms, or a substituted or unsubstituted arylene group
of 6-30 carbon atoms; $R_5$ is

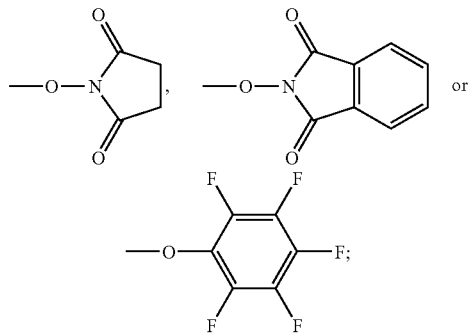

and
d is an integer from 10 to 100,000.

2. The hydrogel copolymer of claim 1, further comprising a repeat unit represented by formula (3):

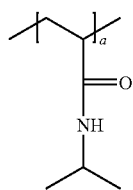

(3)

where a is an integer from 10 to 100,000.

3. The hydrogel copolymer of claim 1, further comprising a repeat unit represented by formula (4):

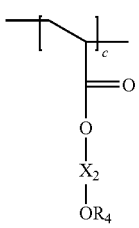

(4)

where $X_2$ is a single bond, O, S, a substituted or unsubstituted alkylene group of 1-20 carbon atoms, a substituted or unsubstituted heteroalkylene group of 1-20 carbon atoms, a substituted or unsubstituted alkenylene group of 2-20 carbon atoms, a substituted or unsubstituted heteroalkenylene group of 2-20 carbon atoms, or a substituted or unsubstituted arylene group of 6-30 carbon atoms; $R_4$ is a hydrogen atom, a halogen atom, a hydroxy group, a substituted or unsubstituted alkyl group of 1-20 carbon atoms, a substituted or unsubstituted alkoxy group of 1-20 carbon atoms, a substituted or unsubstituted alkenyl group of 1-20 carbon atoms, a substituted or unsubstituted aryl group of 6-30 carbon atoms, a substituted or unsubstituted aryloxy group of 6-30 carbon atoms, a substituted or unsubstituted heteroaryl group of 2-30 carbon atoms, or a substituted or unsubstituted heteroaryloxy group of 2-30 carbon atoms; and
c is an integer from 10 to 100,000.

4. A hydrogel copolymer comprising repeat units represented by formulae (1) to (4):

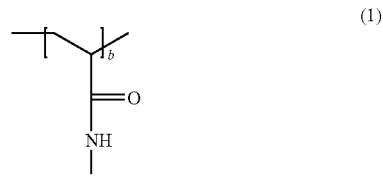

(1)

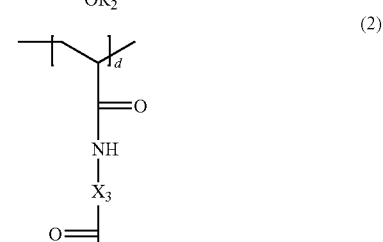

(2)

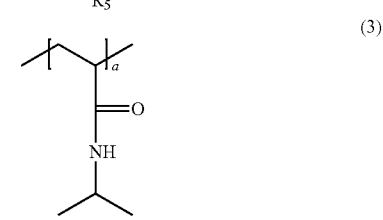

(3)

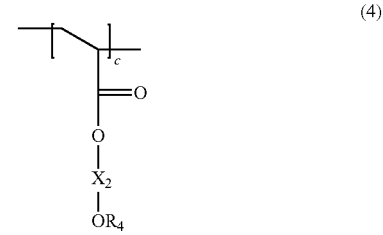

(4)

where $X_1$ is a single bond, O, S. a substituted or unsubstituted alkylene group of 1-20 carbon atoms, a substituted or unsubstituted heteroalkylene group of 1-20 carbon atoms, a substituted or unsubstituted alkenylene group of 2-20 carbon atoms or a substituted or unsubstituted arylene group of 6-30 carbon atoms;.$R_1$ $R_2$ and $R_3$ are each independently a hydrogen atom, a halogen atom, a hydroxy group, a substituted or unsubstituted alkyl group of 1-20 carbon atoms, a substituted or unsubstituted alkoxy group of 1-20 carbon atoms, a substituted or unsubstituted alkenyl group of 1-20 carbon atoms, a substituted or unsubstituted aryl group of 6-30 carbon atoms, a substituted or unsubstituted aryloxy group of 6-30 carbon atoms, a substituted or unsubstituted heteroaryloxy group of 2-30 carbon atoms, or a substituted or unsubstituted heteroarloxy group of 2-30 carbon atoms; and b is an integer from 10 to 100 000 where $X_2$ is a single bond. O, S. a substituted or unsubstituted alkylene group of 1-20 carbon atoms, a substituted or unsubstituted heteroalkylene group of 1-20 carbon atoms, a substituted or unsubstituted alkenylene group of 2-20 carbon atoms, a substituted or unsubstituted heteroalkenylene group of 2-20 carbon atoms. or a substituted or unsubstituted arylene group of 6-30 carbon atoms: $R_4$ is a hydrogen atom, a halogen atom. a hydroxy group, a substituted or unsubstituted alkyl group of 1-20 carbon atoms, a substituted or unsubstituted alkoxy group of 1-20 carbon atoms, a substituted or unsubstituted alkenyl group of 1-20 carbon atoms, a substituted or unsubstituted aryl group of 6-30 carbon atoms, a substituted or unsubstituted aryloxy group of 6-30 carbon atoms, a substituted or unsubstituted heteroaiyl group of 2-30 carbon atoms, or a substituted or unsubstituted heteroaryloxy group of 2-30 carbon atoms; and c is an integer from 10 to 100.000.

where $X_{.3}$ is a single bond, O, S. a substituted or unsubstituted alkylene group of 1-20 carbon atoms, a substituted or unsubstituted heteroalkylene group of 1-20 carbon atoms, a substituted or unsubstituted alkenylene group of 2-20 carbon atoms, a substituted or unsubstituted heteroalkenylene group of 2-20 carbon atoms, or a substituted or unsubstituted atylene group

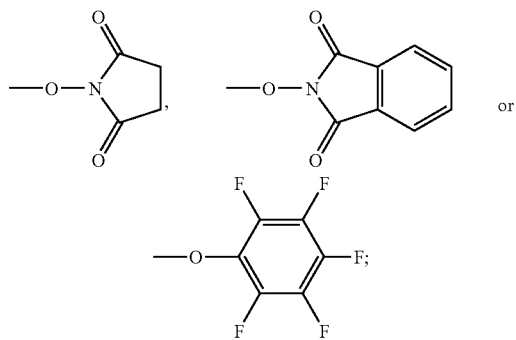

of 6-30 carbon atoms; $R_5$ is;and d is an integer from 10 to 100.000, where a is an integer from 10 to 100.000.

5. A method of selectively removing a material having an amino group from a sample, the method comprising:
   coating the hydrogel copolymer of claim 1 on a substrate having nanopores;
   reacting the hydrogel copolymer with the sample including the material having the amino group; and
   eluting an unreacted sample.

6. The method of claim 5, wherein the material having the amino group is a protein.

7. A substrate for a microarray coated with the hydrogel copolymer of claim 1.

8. The substrate of claim 7, selected from the group consisting of glass, a silicon wafer, plastic, polystyrene, a membrane, and a metal plate.

9. The substrate of claim 7, wherein coating of the hydrogel copolymer on the substrate is carried out through a reaction between alkoxysilane and an OH group on the substrate.

10. A microarray in which biomolecules are immobilized on a hydrogel copolymer of the substrate of claim 7.

11. The microarray of claim 10, wherein the biomolecule is a protein or nucleic acid.

12. A method of producing a microarray, the method comprising:
   coating the hydrogel copolymer of claim 1 on a substrate; and
   coupling the coated hydrogel copolymer to biomolecules to immobilize the biomolecules on the substrate.

13. The method of claim 12, wherein the biomolecule is a protein or nucleic acid.

14. A method of selectively removing a material having an amino group from a sample, the method comprising:
   coating the hydrogel copolymer of claim 2 on a substrate having nanopores;
   reacting the hydrogel copolymer with the sample including the material having the amino group; and
   eluting an unreacted sample.

15. A method of selectively removing a material having an amino group from a sample, the method comprising:
   coating the hydrogel copolymer of claim 3 on a substrate having nanopores;
   reacting the hydrogel copolymer with the sample including the material having the amino group; and
   eluting an unreacted sample.

16. A method of selectively removing a material having an amino group from a sample, the method comprising:
   coating the hydrogel copolymer of claim 4 on a substrate having nanopores;
   reacting the hydrogel copolymer with the sample including the material having the amino group; and
   eluting an unreacted sample.

17. The method of claim 14, wherein the material having the amino group is a protein.

18. The method of claim 15, wherein the material having the amino group is a protein.

19. The method of claim 16, wherein the material having the amino group is a protein.

20. A substrate for a microarray coated with the hydrogel copolymer of claim 2.

21. A substrate for a microarray coated with the hydrogel copolymer of claim 3.

22. A substrate for a microarray coated with the hydrogel copolymer of claim 4.

23. The substrate of claim 20, selected from the group consisting of glass, a silicon wafer, plastic, polystyrene, a membrane, and a metal plate.

24. The substrate of claim 21, selected from the group consisting of glass, a silicon wafer, plastic, polystyrene, a membrane, and a metal plate.

25. The substrate of claim 22, selected from the group consisting of glass, a silicon wafer, plastic, polystyrene, a membrane, and a metal plate.

26. The substrate of claim 22, wherein coating of the hydrogel copolymer on the substrate is carried out through a reaction between alkoxysilane and an OH group on the substrate.

27. The substrate of claim 21, wherein coating of the hydrogel copolymer on the substrate is carried out through a reaction between alkoxysilane and an OH group on the substrate.

28. The substrate of claim 22, wherein coating of the hydrogel copolymer on the substrate is carried out through a reaction between alkoxysilane and an OH group on the substrate.

29. A microarray in which biomolecules are immobilized on a hydrogel copolynfer of the substrate of claim 20.

30. A microarray in which biomolecules are immobilized on a hydrogel copolymer of the substrate of claim 21.

31. A microarray in which biomolecules are immobilized on a hydrogel copolymer of the substrate of claim 22.

32. The microarray of claim 29, wherein the biomolecule is a protein or nucleic acid.

33. The microarray of claim 30, wherein the biomolecule is a protein or nucleic acid.

34. The microarray of claim 31, wherein the biomolecule is a protein or nucleic acid.

35. A method of producing a microarray, the method comprising:
   coating the hydrogel copolymer of claim 2 on a substrate; and
   coupling the coated hydrogel copolymer to biomolecules to immobilize the biomolecules on the substrate.

36. A method of producing a microarray, the method comprising:
   coating the hydrogel copolymer of claim 3 on a substrate; and
   coupling the coated hydrogel copolymer to biomolecules to immobilize the biomolecules on the substrate.

37. A method of producing a microarray, the method comprising:
   coating the hydrogel copolymer of claim 4 on a substrate; and
   coupling the coated hydrogel copolymer to biomolecules to immobilize the biomolecules on the substrate.

38. The method of claim 35, wherein the biomolecule is a protein or nucleic acid.

39. The method of claim 36, wherein the biomolecule is a protein or nucleic acid.

40. The method of claim 37, wherein the biomolecule is a protein or nucleic acid.

* * * * *

UNITED STATES PATENT AND TRADEMARK OFFICE
CERTIFICATE OF CORRECTION

PATENT NO. : 7,572,644 B2
APPLICATION NO. : 11/334145
DATED : August 11, 2009
INVENTOR(S) : Lee et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 476 days.

Signed and Sealed this

Fourteenth Day of December, 2010

David J. Kappos
*Director of the United States Patent and Trademark Office*